United States Patent [19]
Katz et al.

[11] Patent Number: 4,604,354
[45] Date of Patent: Aug. 5, 1986

[54] IMMOBILIZED GLUCOSE ISOMERASE CONTAINING MICROBIAL CELLS

[75] Inventors: Edward Katz, St. Louis; Jon J. Benedicktus, Oakland; Edward L. Knarr, St. Louis; Barrett L. Scallet, Clayton, all of Mo.

[73] Assignee: Busch Industrial Products Corporation, St. Louis, Mo.

[21] Appl. No.: 724,074

[22] Filed: Apr. 17, 1985

Related U.S. Application Data

[63] Continuation of Ser. No. 400,890, Jul. 22, 1982, abandoned.

[51] Int. Cl.$^4$ .................. C12P 19/24; C12N 11/00; C12N 11/14; C12N 11/02
[52] U.S. Cl. ................................ 435/94; 435/174; 435/176; 435/177
[58] Field of Search ............... 435/94, 174, 176, 177

[56] References Cited

U.S. PATENT DOCUMENTS 4,242,451 12/1980 Ehrenthal et al. .................. 435/94
4,289,853 9/1981 Bailey et al. ....................... 435/177

OTHER PUBLICATIONS

Liu, et al., Biotechnology and Bioengineering, vol. XVII, 1957, pp. 1695-1696.
Cho, et al., Biotechnology and Bioengineering, vol. XX, 1978, pp. 1651-1665.

Primary Examiner—Dvaid M. Naff
Attorney, Agent, or Firm—Gravely, Lieder & Woodruff

[57] ABSTRACT

An immobilized glucose isomerase having increased productivity and stability is prepared by mixing a smectite filler and 50-100 mesh granular activated carbon with flocculated cells of an organism of the genus Actinoplanes and forming the resulting mixture into discrete particles.

10 Claims, No Drawings

IMMOBILIZED GLUCOSE ISOMERASE CONTAINING MICROBIAL CELLS

This application is a continuation of Ser. No. 400,890 filed 7-22-82, now abandoned.

BACKGROUND OF THE INVENTION

This invention relates to immobilized glucose isomerase, and particularly relates to the treatment of a flocculated homogenate of whole cell glucose isomerase, derived from microorganisms of the Actinoplanes genus, with a combination of milled granular carbon of about 50-100 mesh size and a smectite filler added prior to drying.

This application involves an improvement of the process and product described in Ehrenthal, Shieh, Scallet and Rajpara, U.S. Pat. No. 4,242,451 issued Dec. 30, 1980, entitled METHOD OF TREATMENT OF FLOCCULATED HOMOGENATE OF MICROBIAL CELLS CONTAINING GLUCOSE ISOMERASE.

U.S. Pat. No. 4,242,451 (assigned to the assignee of this invention) discloses a process for treating a flocculated homogenate of whole cell glucose isomerase derived from microorganisms of the Actinoplanes genus in order to dry the homogenate so that the enzyme is immobilized and usable in converting glucose to fructose. The critical step in the process of U.S. Pat. No. 4,242,451 is the addition of a water absorbing smectite filler to the flocculated homogenate prior to drying and/or extrusion. The system of U.S. Pat. No. 4,242,451 basically mixes a concentrated flocculated homogenate with prescribed amounts of bentonite, extrudes this material, dries it, mills it and screens the immobilized glucose isomerase to the appropriate mesh size. The immobilized glucose isomerase from U.S. Pat. No. 4,242,451 has a half life of 50-60 days at 60° C. and a productivity of 5000-6000 lbs. dry weight high levulose syrup (HLS) per lb. of immobilized glucose isomerase as is, for the first half life of the enzyme.

One of the principal objects of the present invention is to significantly reduce the cost of immobilized glucose isomerase compared to that made by the process of U.S. Pat. No. 4,242,451. Another object is to improve the properties of immobilized glucose isomerase as compared to the properties of the immobilized glucose isomerase made by the process of U.S. Pat. No. 4,242,451.

As noted in the specification of U.S. Pat. No. 4,242,451 there are several prior patents which discuss the flocculation of glucose isomerase cells with various flocculation agents. These processes, as noted in U.S. Pat. No. 4,242,451, are not suitable for use with microorganisms of the Actinoplanes genus, because the Actinoplanes cells are difficult to dry and are difficult to extrude since they retain a large amount of water. The retained water cannot be removed effectively by conventional drying means.

Among the patents noted as prior art in U.S. Pat. No. 4,242,451 are:

Aotz et al, U.S. Pat. No. 3,980,521 which discloses a method of preparing a water insoluble glucose isomerase product by concentrating and homogenizing microorganism cells to form a homogenized cell concentrate containing ruptured cells, reacting the homogenized concentrate with glutaraldehyde to form a coherent solid product, and removing water and shaping the coherent product into a divided form.

Lee et al, U.S. Pat. No. 3,821,086 discloses a process for converting glucose to fructose by contacting a glucose substrate with flocculated whole microbial cells containing glucose isomerase. The whole microbial cells are previously flocculated by means of a polyelectrolyte flocculating agent.

Long, U.S. Pat. No. 3,989,596 discloses a method of forming an enzyme-containing aggregate comprising the steps of flocculating microbial cells and their associated enzymes with a synthetic polyelectrolyte flocculating agent, and drying the aggregate.

Lee, U.S. Pat. No. 3,989,597 discloses a method of forming an enzyme-containing aggregate comprising the steps of flocculating microbial cells and their associated enzymes with a synthetic polyelectrolyte flocculating agent, freezing the aggregate, then thawing and crushing the aggregate.

Lee, U.S. Pat. No. 3,821,086, Long, U.S. Pat. No. 3,989,596, and Lee, U.S. Pat. No. 3,989,597 also state that the flocculated cells may be extruded into various shapes suitable for use in an enzymatic process.

In U.S. Pat. No. 4,242,451, water retention of organism of the Actinoplanes genus was attacked by the addition of a smectite filler to the flocculated homogenate prior to drying and/or extrusion.

In the present process we have unexpectedly discovered that adding 50-100 mesh milled granular carbon to the flocculated homogenate increases the productivity of the immobilized glucose isomerase by about 100% compared to the product of U.S. Pat. No. 4,242,451.

The recently issued U.S. Pat. No. 4,289,853 to Barley et al is entitled "HIGH LOADING OF IMMOBILIZED ENZYMES ON ACTIVATED CARBON SUPPORTS" and relates to the treatment of activated carbon with carbodiimide or an isoxazolium salt to form active organic radicals on the surface of the carbon followed by treatment of the reacted carbon with an enzyme to immobilize the enzyme on the carbon support by displacing the salt or the carbodiimide and resulting in a carbon-enzyme product. U.S. Pat. No. 4,289,853 also discusses the state of the art as to using carbon in enzyme immobilizing techniques.

It should be noted that U.S. Pat. No. 4,242,451 suggests adding carbon to the smectite filler to increase porosity of the extruded product (col. 2, lines 52-54). Also Tables III and IV of U.S. Pat. No. 4,242,451 show addition of carbon (Darco G-60 from ICI-USA). This carbon is stated to increase available activity as compared to filter aid (Celite 560 from Johns-Manville). However, Darco G-60 is powdered carbon with 70% passing through 325 mesh screen. Conventional granular carbon is accepted to be 12-30 or 40 mesh.

We have found that when the granular carbon is milled to 50-100 mesh and added in an amount of about 5% to about 55% by weight based on the weight of the dry solids of the total mass prior to extrusion and/or drying which includes the smectite, we obtain an unexpected improvement in productivity and stability (half-life) of the immobilized glucose isomerase.

SUMMARY OF THE INVENTION

The present invention comprises an immobilized glucose isomerase containing a combination of a smectite and granular carbon of about 50-100 mesh. The addition of the 50-100 mesh carbon increases the productivity and stability of immobilized glucose isomerase and is particularly useful with enzymes from organisms of the Actinoplanes genus. This invention is an improvement of the process and product covered in U.S. Pat. No. 4,242,451.

DETAILED DESCRIPTION

Whole microbial cells containing glucose isomerase are prepared from microorganisms of the genus Actinoplanes, more specifically, *Actinoplanes missouriensis*. Methods for growing these cells are disclosed in U.S. Pat. Nos. 3,834,988, 3,992,262 and 4,003,793.

A whole cell slurry is then homogenized in such a way that a substantial proportion of the cells is disrupted. The slurry is preferably passed through a Manton-Gaulin homogenizer 1 to 3 times at a pressure of 2000–9000 psi. Means other than homogenization may be used to disrupt the cells.

A flocculant is then added to the homogenate. Flocculants suitable for this invention are cationic polyelectrolytes. Preferred flocculants are Cat-floc from Calgon Co. and Magnifloc 581C from American Cyanamid Co. The concentration of flocculant should range from 20% to 90% based on the dry weight of the cells.

The flocculated homogenate is collected by centrifugation and dewatered to a level of about 15% to about 30% solids.

A water absorbing filler is then added to the flock. The addition of filler allows effective extrusion. Suitable fillers include bentonite, montmorillonite, and other clays of the smectite group.

Darco granular carbon was ground in a Wiley Mill or hammer mill and sieved to about 50 to about 100 mesh. This was added to the floc in combination with the smectite. About 5% to about 55% carbon and about 5% to about 15% smectite are added on a dry solids basis, based on the weight of the total composite mixture.

In a preferred embodiment of the invention the dewatered filler and carbon treated enzyme-containing floc can be extruded without difficulty through dies having clyindrical openings of about 1 to about 2 mm. diameter. The extruded particles are dried, preferably in an air oven or fluidized bed drier at 120°–150° F.

The cylindrical particles are then milled and sieved to a granular shape. These granules have a preferred mesh size of about 16–20 mesh (0.8–1.2 mm.).

For use, the granular particles are packed into a jacketed column, which is maintained at about 60° to 65° C. A 98 D.E. ion exchanged syrup solution of about 35 to 50% dry solids, and about pH 7.5, containing about 7 mM $Mg^{++}$ and about 250 ppm $SO_2$ is pumped continuously through the column, and the product analyzed for fructose. From this analysis the half-life of the particles can be determined. The half-life at 60° C., may be as long as about 110–120 days, compared to half-life of 50–60 days for a standard preparation containing no carbon.

Following in Table No. 1 are results from runs made in a 1″ diameter column with a 5⅝″ high bed of immobilized glucose isomerase made according to the hereinbefore discussed procedure. The feed was 97 D.E. dextrose ion exchanged syrup at 140° F. (60° C.) and the product recovered was 42% fructose syrup.

TABLE NO. 1

| EXAMPLE NO. | 1 | 2 | 3 | 4 | STANDARD PREP. |
|---|---|---|---|---|---|
| Mesh Size Dried Granules | 16–20 | 16–20 | | 16–20 | 16–20 |
| Composition Dried Granules | | | | | |
| Cell Floc (DSB) Contains *Actinoplanes missouriensis* | 80% | 66.2% | 42% | 66.4% | 88.9% |
| Bentonite | 10% | 8.2% | 5.4% | 8.6% | 11.1% |
| 50–100 Mesh Carbon | 10% | 25.6% | 52.6% | 25.9% | — |
| Activity IGIU/gm Total DSB | 852 | 770 | 655 | 800 | 650–800 |
| Actual Days Column Operation | 40 | 40 | — | — | — |
| Projected Half-Life (days) | 120 | 110 | | | 50–60 (Actual) |

The standard preparation is the enzyme from *Actinoplanes missouriensis* mixed with floc and bentonite as described in U.S. Pat. No. 4,242,451 and the activity and half-life are the averages for many runs made using these conditions.

It is seen that using up to 52.6% carbon still allows an activity of about 650 IGIU/gram of total dry solids on a dry solids basis (Example No. 3). This is attainable even though the amount of cell floc is only 42% compared to almost 89% cell floc in a standard preparation of comparable activity. As the enzyme is costly, this reduces the cost per unit of enzyme compared to standard preparation, and combined with the longer half-life noted in Examples 1 and 2, substantially reduces the cost of the enzyme per pound of syrup produced.

The IGIU is a measure of the amount of enzyme which will produce a given amount of fructose from glucose under stated conditions. When this is compared to the total weight of dry solids in the immobilized enzyme, there is created a basis for comparing the efficiency of the enzyme preparation as the immobilized enzyme is sold on a weight and activity/gm dry solids basis including the filler.

EXAMPLE NO. 5

An immobilized glucose isomerase was prepared as hereinbefore discussed with 66.2% cell floc, 8.2% bentonite and 25.5% of 50–100 mesh activated carbon. The mesh size of the extruded particles of immobilized glucose isomerase was 16–20. The enzyme is from *Actinoplanes missouriensis* (as it was in examples 1-4 of Table 1).

The column has a 1×5⅝ inch bed of immobilized enzyme in syrup and the feed was ion exchanged 97 DE. glucose syrup at 140° F. The time of this run was 94 days and the product was 42% fructose syrup.

At the end of the 94 days, the activity was 372 IGIU compared to an initial activity of approximately 700 IGIU. A summary of results for this run is shown in Table No. 2.

TABLE NO. 2

Test Column - 1"0 × 5⅝" Bed, 14 grams
91.8% Dry Substance IGI in Column Temp. = 140° F., pH 7.5

| Days | Av. % Fructose for Time Period | Av. Flow cc/min. | Av. Dry Substance Staley Dextrose 98 De Feed Syrup % | Total Grams 42% Fructose HLS Dry Substance Per Time Period (Quantity Adjusted to 42% Fructose Basis) |
|---|---|---|---|---|
| 1-10 | 41.6 | 2.87 | 42.6 | 20,570 |
| 11-20 | 40.7 | 2.26 | 42.5 | 15,821 |
| 21-30 | 42.2 | 2.00 | 42.3 | 14,443 |
| 31-40 | 40.0 | 2.26 | 42.1 | 15,405 |
| 41-50 | 41.0 | 1.84 | 42.5 | 12,982 |
| 51-60 | 41.6 | 1.86 | 42.7 | 13,389 |
| 61-70 | 41.9 | 1.88 | 42.4 | 13,496 |
| 71-80 | 40.4 | 1.75 | 42.3 | 12,099 |
| 81-90 | 40.4 | 1.62 | 42.3 | 11,187 |
| 91-94 | 39.4 | 1.79 | 42.1 | 4,818 |
| | | | 94 Day Total | 134,210 gram |

Productivity - 134,210/14 = 9586 Gram 42% HLS-DSB/Gram IGI (As Is)
Activity at end of 94 days = 372 IGIU - First half-life not yet reached.
Estimated productivity to first half-life (360 IGIU) = 10,000 lbs. HLS/lb. IGI.

In measuring the productivity of an enzyme, the standard of measure in the industry is the number of pounds of high levulose syrup (42% levulose) that are produced per pound of enzyme used.

The half-life of an enzyme is that point in time where it has lost one half of its original activity. The total estimated useful life of an immobilized enzyme is usually calculated to be three (3) half lives.

What is claimed is:

1. A method of immobilizing glucose isomerase cell material obtained from whole microbial cells of an organism of the genus Actinoplanes containing glucose isomerase comprising the steps of:
   a. preparing whole microbial cells of an organism of the genus Actinoplanes containing glucose isomerase,
   b. disrupting a substantial portion of said whole cells,
   c. adding a flocculant to said disrupted glucose isomerase cell material,
   d. recovering and dewatering the flocculated cell material,
   e. adding to said dewatered flocculated glucose isomerase cell material from about 3% to about 15% of a water absorbing smectite filler and about 5% to about 55% granular activated carbon of about 50 to about 100 mesh, both by weight of total composite mixture on a dry solids basis, and
   f. forming the mixture of glucose isomerase cell material and the water absorbing smectite filler and granular activated carbon into discrete particles.

2. The method of claim 1 wherein the microorganism is *Actinoplanes missouriensis*.

3. The method of claim 1 including the step of extruding the mixture of glucose isomerase cell material and smectite filler and carbon through a die, and milling and screening the extruded particles to a particle size smaller than 12 mesh.

4. The method of claim 1 including the step of drying the mixture of glucose isomerase cell wall material and smectite filler and carbon and grinding the dried particles to about 16 to about 20 mesh.

5. The method of claim 1 wherein the immobilized glucose isomerase cell material from step f is contacted with a solution of glucose to convert the glucose to fructose.

6. The method of claim 5 wherein said cell material is derived from *Actinoplanes missouriensis*.

7. An immobilized glucose isomerase cell material in the form of discrete particles prepared by the process of claim 1.

8. The immobilized glucose isomerase cell material of claim 7 wherein the cells are derived from *Actinoplanes missouriensis*.

9. The immobilized glucose isomerase cell material of claim 7 wherein the discrete particles are about 12-100 mesh in size.

10. The immobilized glucose isomerase cell material of claim 7 wherein the particles are about 16 to about 20 mesh in size.

* * * * *